(12) United States Patent
Hayakawa et al.

(10) Patent No.: US 6,294,151 B1
(45) Date of Patent: Sep. 25, 2001

(54) ISOTOPIC UREA TABLETS

(75) Inventors: Eiji Hayakawa; Shigemitsu Miura, both of Susono; Kunio Ito, Sunto-gun; Kuniaki Sakato, Atsugi, all of (JP)

(73) Assignee: Kyowa Hakko Kogyo, Co., Ltd., Tokyo (JP)

( * ) Notice: Subject to any disclaimer, the term of this patent is extended or adjusted under 35 U.S.C. 154(b) by 0 days.

(21) Appl. No.: 09/051,211

(22) PCT Filed: Aug. 12, 1997

(86) PCT No.: PCT/JP97/02809

§ 371 Date: Apr. 3, 1998

§ 102(e) Date: Apr. 3, 1998

(87) PCT Pub. No.: WO98/06442

PCT Pub. Date: Feb. 19, 1998

(30) Foreign Application Priority Data

Aug. 13, 1996 (JP) ...................................................... 8-213350

(51) Int. Cl.[7] .......................... A61K 51/00; A61M 36/14
(52) U.S. Cl. ...................... 424/1.81; 424/1.65; 424/1.61; 424/1.11
(58) Field of Search ................... 424/1.11, 1.29, 424/1.37, 1.61, 1.65, 1.81; 548/316.4; 528/259; 564/32, 64; 558/8

(56) References Cited

U.S. PATENT DOCUMENTS

| 3,885,026 | 5/1975 | Heinemann et al. . |
|---|---|---|
| 4,181,621 | 1/1980 | Raaf et al. . |
| 4,830,010 | 5/1989 | Marshall . |
| 5,643,591 | * 7/1997 | Mehra et al. ........................ 424/408 |
| 6,067,989 | * 5/2000 | Katzman ............................. 128/898 |

FOREIGN PATENT DOCUMENTS

| 294634 | * 10/1991 | (DE) . |
|---|---|---|
| 6-72878 | 3/1994 | (JP) . |
| 6-135847 | 5/1994 | (JP) . |
| 9212633 | * 8/1992 | (WO) . |
| 96/14091 | 5/1996 | (WO) . |

OTHER PUBLICATIONS

The Merck Index, pp. 274 (Entry No. 1814), 464 (Entry No. 2925), 759 (Entry No. 4719), 1044 (Entry No. 6522), and 1101 (Entry No. 6917), 1989.*

"Comprehensive Technology for the System of Developing New Pharmaceutical Preparations—Bases and Additives" (English Translation); Edited by Sadao Iguchi; (1985) R&D Planning; p. 410–411; 417–419;

The American Journal of Gastroenterology, vol. 91; No. 2, 1996, pp. 233–238 Peura et al.

Marshall et al Gastroenterology; vol. 100, No. 5, May 1991, p. A11B, XP000199432.

* cited by examiner

Primary Examiner—Dameron L. Jones
(74) Attorney, Agent, or Firm—Antonelli, Terry, Stout & Kraus, LLP

(57) ABSTRACT

The present invention provides a tablet containing isotope-labeled urea and an inorganic compound.

57 Claims, No Drawings

ISOTOPIC UREA TABLETS

TECHNICAL FIELD

The present invention relates to a tablet containing isotope-labeled urea for diagnosing the infection with urease-generating bacteria, particularly *Helicobacter pylori*.

BACKGROUND ART

Because *Helicobacter pylori* has strong urease-producing activity, urea labeled with $^{13}C$ or $^{14}C$ is used for diagnosing stomach infected with *Helicobacter pylori*. Urea labeled with $^{13}C$ or $^{14}C$ is prepared as powder, particularly freeze-dried powder, containing urea alone, for oral administration in aqueous solution. The urea labeled with 13C or 14C is degraded by the urease produced by *Helicobacter pylori* in stomach into carbon dioxide gas labeled with $^{13}C$ or 14C, which is then released into expired air. By measuring the concentration of the carbon dioxide labeled with $^{13}C$ or $^{14}C$, therefore, the presence or absence of *Helicobacter pylori* infection can be diagnosed. When the powder is orally given in aqueous solution, the urea labeled with $^{13}C$ or $^{14}C$ is degraded with urease derived from oral bacterial flora, which causes difficulty in diagnosing correctly *Helicobacter pylori* infection.

As urea formulations for, diagnosing *Helicobacter pylori* infection, a capsule of $^{14}C$-urea [The American Journal of Gastroenterology, 91, 233 (1996)] and a substantially water-soluble composition in solid, containing urea labeled with an isotope (W096/14091), have been known.

However, urea has strong cohesion potency and therefore sticks to tableting machines and the like during the tableting process, which results in poor industrial productivity. Tablets containing urea have so poor hardness that it is difficult to produce high-quality tablets of urea.

DISCLOSURE OF INVENTION

The present inventors have found that an urea tablet with practical disintegration time and sufficient hardness can be produced by mixing urea with one or several additives among various additives of inorganic compounds and then formulating the mixture into tablet, thereby preventing the stickiness due to the cohesion potency of urea.

The present invention relates to a tablet containing isotope-labeled urea and an inorganic compound, which may further contain an organic compound or a disintegrant.

Urea with no label is generally composed of carbon atoms of a mass number of 12, oxygen atoms of a mass number of 16, nitrogen atoms of a mass number of 14 and hydrogen atoms of a mass number of 1. The term "isotope-labeled urea" in the present invention means urea labeled with an isotope of at least one of carbon atom, oxygen atom, nitrogen atom and hydrogen atom, the isotope having a different mass number from the aforementioned mass number of the corresponding atom or a mixture of urea labeled with the isotope and urea with no label. The urea labeled includes preferably urea labeled with $^{13}C$, $^{14}C$ or $^{18}O$, and more preferably $^{13}C$ or $^{14}C$. In the present invention, for example, urea labeled with $^{13}C$ is represented as $^{13}C$-urea.

The inorganic compound includes, for example, inorganic compounds containing silica such as silicic acid anhydride, silicic acid, and silicate; inorganic compounds containing calcium; and inorganic compounds containing aluminium. The silicic acid includes, for example, ortho-silicic acid, meta-silicic acid, meso-disilicic acid, meso-trisilicic acid and meso-tetrasilicic acid. The silicate includes, for example, metal salts of silicic acid. The metal forming silicate includes, for example, aluminum, zinc, potassium, calcium and sodium. The inorganic compounds containing calcium include for example calcium salts. Specific examples include, for example, calcium carbonate, calcium hydrogen phosphate, calcium hydroxide, calcium chloride, calcium sulfate, and calcium nitrate. The inorganic compounds containing aluminium include, for example, aluminium salts, specifically including, for example, aluminum hydroxide and aluminum chloride.

Among these inorganic compounds, preferred are inorganic compounds containing silica and inorganic compounds containing aluminium; and more preferred are inorganic compounds containing silica. As the inorganic compounds containing silica, preferred is silicic acid anhydride; and more preferred is light anhydrous silicic acid.

The organic compound includes, for example, sugars, amino acids, protein, nucleic acid, and organic acids. The sugars include, for example, polysaccharides such as starch, cellulose, chitin and chitosan; oligosaccharides such as lactose and sucrose; monosaccharides such as mannitol and glucose. As the cellulose, preferred is crystal cellulose. The amino acids include naturally occurring α-amino acids such as glycine, glutamic acid, glutamine, lysine, aspartic acid, and asparagine. The protein includes, for example, globulin and albumin. The nucleic acid includes, for example, inosinic acid, adenylic acid, thymidynic acid, guanylic acid and cytidylic acid. The organic acids include, for example, lactic acid, acetic acid and citric acid. As the organic compound, preferred are sugars such as mannitol, lactose and crystal cellulose.

One example of the tablet of the present invention comprises the isotope-labeled urea and such inorganic compound. The content of the isotope-labeled urea is 2 to 2,000 mg, preferably 20 to 350 mg per one tablet. The content of the inorganic compound is 0.1 to 200 parts by weight, preferably 0.5 to 100 parts by weight, and more preferably 1 to 50 parts by weight based on 100 parts by weight of the isotope-labeled urea.

The tablet of the present invention may optionally contain the organic compound. More preferably, the tablet contains the isotope-labeled urea, the inorganic compound and the organic compound. The content of the organic compound is 0 to 1000 parts by weight, preferably 10 to 500 parts by weight, and more preferably 100 to 300 parts by weight based on 100 parts by weight of the isotope-labeled urea in the tablet.

The tablet of the present invention may optionally contain a disintegrant. In respect of the shortened disintegration time after the administration of the tablet, it is preferable that the tablet contains the isotope-labeled urea, the inorganic compound and the disintegrant or that the tablet contains the isotope-labeled urea, the inorganic compound, the organic compound and the disintegrant. The disintegration time of the tablet containing the disintegrant can be adjusted, depending on the amount of the disintegrant to be added. The disintegration time of the tablet of the present invention in stomach is 5 seconds to 10 minutes, preferably 10 seconds to 2 minutes, and particularly preferably 15 seconds to 60 seconds. The disintegration time can be measured according to the Disintegration Test of the Japanese Pharmacopoeia.

Any disintegrant for use in formulation may be used, with no specific limitation, including, for example, polyplasdone, low-substituted hydroxypropyl cellulose, croscarmellose sodium, carboxymethyl cellulose and the calcium salt thereof, hydroxypropyl starch and the like; preferred examples are polyplasdone and low-substituted hydroxypropyl cellulose.

The content of the disintegrant is 0 to 500 parts by weight, preferably 1 to 100 parts by weight and more preferably 3 to 20 parts by weight based on 100 parts by weight of the isotope-labeled urea in the tablet.

Additionally, the tablet of the present invention may optionally contain other additives frequently used for the formulation of other tablets, such as, lubricants, coloring agents, sweetening agents, antioxidants and binders.

The lubricants include for example magnesium stearate, calcium stearate, zinc stearate, stearic acid, talc, hydrogenated vegetable oil, and talc.

Example of the coloring agents include yellow ferric oxide, iron sesquioxide, various edible dyes, and sodium copper chlorophyllin.

Example of the sweetening agents include sucrose, saccharin, aspartame, mannitol, dextran, lemon flavor, menthol, and citric acid.

Example of the antioxidants include ascorbic acid and reduced-type glutathione.

Example of the binders include polyvinyl alcohol, polyvinyl pyrrolidone, methyl cellulose, hydroxypropyl cellulose, hydroxypropyl methyl cellulose, hydroxyethyl cellulose, starch, dextrin, $\alpha$-type starch, pullulan, gum arabic, agar, gelatin, and purified sugar; preferred is hydroxypropyl cellulose.

By firstly preparing a tablet of a lens shape (of a diameter of 8.5 mm $\emptyset$) by a rotary tableting machine (Correct 12HUK,, manufactured by Kikusui Seisakusho) and subjecting the tablet to a disintegration test in the test solution No. 1 (artificial gastrointestinal fluid, pH 1.2) according to the Disintegration Test of the Japanese Pharmacopoeia, the hardness of the tablet of a disintegration time of 120 seconds is measured by a tablet break strength tester (TH-203CP, manufactured by Toyama Industry). The tablet of the present invention has hardness of preferably 5 kgf or more, more preferably 10 kgf. If the disintegration time of the tablet is 60 seconds, the tablet is of hardness of preferably 4 kgf or more, more preferably 8 kgf or more. If the disintegration time of the tablet is 30 seconds, the tablet is of hardness of preferably 3 kgf or more, more preferably 6 kgf or more.

The method for producing the tablet of the present invention is described below.

Tablet of the present invention, which is characterized in that the stickiness of urea can be prevented, is produced by mixing the urea with the inorganic compound and, if necessary, the organic compound, and if necessary, grinding the resulting mixture. The mixing may be carried out by routine mixing procedures, by a mixer for example V-type blender. The grinding is also carried out by routine grinding procedures by means of grinders, for example sample mill grinder.

The average particle size of the ground product is preferably 100 $\mu$m or less, particularly preferably 50 $\mu$m or less.

By mixing the urea with the inorganic compound and if necessary, the organic compound, and, if necessary, grinding the resulting mixture, the mixture or the ground mixture can be formulated into a tablet by routine industrial tableting process with no use of any specific tableting process. More specifically, by mixing the urea with the inorganic compound, the cohesion potency of the urea and the stickiness due to the potency onto formulation machines such as tableting machine can be prevented, resulting in the improvement of the industrial productivity.

The tablet can be produced by mixing the isotope-labeled urea with the inorganic compound and, if necessary, additives including the organic compound, the disintegrant and the lubricants, in a mixer, and, if necessary, grinding the resulting mixture by means of grinder to directly tablet the resulting mixture in powder or the ground mixture by a tableting machine and the like or press the mixture by a hydraulic pressing machine. Preferably, the tablet containing the organic compound or the disintegrant may be prepared, by preliminarily mixing them with a binder by dry or wet process and, if necessary, grinding the mixture, and subsequently tableting the mixture. For example, the tablet can be produced by mixing the isotope-labeled urea, the inorganic compound and the organic compound or the disintegrant together in a mixer and, if necessary, grinding the resulting mixture, then adding a binder in aqueous solution or ethanol solution for granulation, drying, and if necessary, adding a lubricant and the like thereto. The concentration of the binder in ethanol solution is preferably 20 w/w % or less.

The resulting tablet may be coated with various coatings and sugar coatings, if necessary.

In order to diagnose the the infection with *Helicobacter pylori* using the tablet of the present invention, isotope-labeled substance, which is discharged, as a metabolite, from the orally administered tablet of the present invention into, for example, expired air, is determined. Generally, $^{13}CO_2$ or $^{14}CO_2$ in expired air is measured by an infrared analyzer or a mass analyzer. In case that the isotope-labeled substance is radioactive such as $^{14}CO_2$, radiation counter may be used.

The effect of the present invention are now described in the following test examples.

Test Example 1

Together with the compounds shown in Table 1, urea was ground and mixed in a mortar. After the process, the presence or absence of urea cohesion was observed. The results are shown in Table 1.

TABLE 1

| Compound | Weight ratio to urea | Cohesion |
| --- | --- | --- |
| Non | — | observed |
| Crystal cellulose | 1.0 | not observed |
| Light anhydrous silicic acid | 1.0 | not observed |
| Light anhydrous silicic acid | 0.5 | not observed |
| Light anhydrous silicic acid | 0.1 | not observed |
| Calcium carbonate | 1.0 | not observed |
| Magnesium aluminate hydrogen phosphate | 1.0 | not observed |
| Aluminium hydroxide | 1.0 | not observed |

By mixing these organic compounds or inorganic compounds with urea, the urea cohesion due to the stickiness of urea can be prevented.

Test Example 2

As shown in Table 2, 100 g of urea was mixed with various inorganic compounds or organic compounds, and the resulting mixture was ground in a grinder (Sample Mill Grinder of Type KEWG-1F, manufactured by Fuji Paudal). The extent of cohesion was observed subsequently. The results are shown in Table 2.

TABLE 2

| urea | mannitol | crystal cellulose | light anhydrous silicic acid | Assessment |
| --- | --- | --- | --- | --- |
| 100 | — | — | — | X |
| 100 | 300 | — | — | ○ |
| 100 | — | 100 | — | ○ |
| 100 | — | 150 | — | ⊙ |
| 100 | — | — | 5 | ○ |
| 100 | — | — | 8 | ⊙ |
| 100 | — | — | 10 | ⊙ |
| 100 | — | 50 | 3 | ○ |
| 100 | — | 100 | 3 | ⊙ |

X: strong cohesion of powder solidified after grinding was observed.
○: slight cohesion of powder after grinding was observed.
⊙: no cohesion of powder after grinding was observed.

Strong cohesion was observed with respect to the resulting ground product of urea alone; the product was at a solidified state such that the product could not be disintegrated even if pushed strongly. However, the product mixed with the inorganic compounds or organic compounds could suppress urea cohesion. If the product of urea alone was ground for a prolonged term, the grinder was overloaded because of sticking of urea. Thus, it is concluded that the stickiness of urea should be prevented for industrially producing tablets containing urea.

Test Example 3

According to the Disintegration Test of the Japanese Pharmacopoeia, the tablets obtained in Examples 4 to 8 were subjected to a disintegration test in test solution No.1 (artificial gastric juice, pH 1.2). The hardness of the tablets was measured by a tablet break strength meter (TH-203CP, manufactured by Toyama Industry). The tablet diameter and thickness were measured by a dial gage (SM-528, manufactured by Teclock). The results are shown in Table 3.

TABLE 3

| Item | Example 4 | Example 5 | Example 6 | Example 7 | Example 8 |
| --- | --- | --- | --- | --- | --- |
| Tablet diameter (mm ø) | 8.5 | 8.5 | 8.5 | 8.5 | 9.0 |
| Tablet thickness (mm) | 4.6 | 4.5 | 4.6 | 4.4 | 5.2 |
| Tablet hardness (kgf) | 7.4 | 4.2 | 6.5 | 7.5 | 8.7 |
| Disintegration time (sec) | 40 | 58 | 55 | 22 | 45 |

The resulting tablets had hardness of 4 kgf or more, with the disintegration times within one minute. Thus, the tablets had excellent properties.

By a hydraulic pressing machine [P-1B, manufactured by Riken Instruments, Co.], the same mixture powders (250 mg) as those in the individual Examples were prepared into tablets by modifying the tableting pressure at 10 kgf, 15 kgf and 20 kgf, to determine the tablet hardness and disintegration time.

TABLE 4

| Tablet compositions | Tablet thickness (mm) | Hardness (kgf) | Disintegration time (sec) |
| --- | --- | --- | --- |
| Examples 4 | 3.84 | 11.6 | 96 |
| Examples 4 | 3.79 | 12.3 | 120 |
| Examples 4 | 3.65 | 18.5 | 186 |
| Examples 5 | 3.84 | 9.6 | 58 |
| Examples 5 | 3.68 | 15.6 | 122 |
| Examples 5 | 3.67 | 17.8 | 178 |
| Examples 6 | 4.20 | 4.3 | 46 |
| Examples 6 | 4.12 | 8.3 | 98 |
| Examples 6 | 4.09 | 9.1 | 114 |
| Examples 7 | 4.07 | 7.1 | 33 |
| Examples 7 | 3.92 | 9.3 | 80 |
| Examples 7 | 3.89 | 10.2 | 88 |
| Examples 8 | 3.69 | 4.3 | 19 |
| Examples 8 | 3.55 | 6.0 | 31 |
| Examples 8 | 3.50 | 5.9 | 39 |

These data were statistically treated. If the disintegration time of each tablet is preset at 30 seconds, the tablets of Examples 4, 5, 6, 7 and 8 can procure individually hardness values of 5.5 kgf, 7.8 kgf, 3.2 kgf, 6.9 kgf and 5.4 kgf, respectively. Hence, it is expected that very hard tablets can be produced. If the disintegration time of each tablet is preset at 60 seconds, the tablets of Examples 4, 5, 6, 7 and 8 can procure individually hardness values of 8.0 kgf, 10.0 kgf, 5.3 kgf, 8.5 kgf and 8.6 kgf, respectively. Hence, it is also expected that very hard tablets can be produced. If the disintegration time of each tablet is preset at 120 seconds, the tablets of Examples 4, 5, 6, 7 and 8 can procure individually hardness values of 13.0 kgf, 14.4 kgf, 9.7 kgf, 11.7 kgf and 15.0 kgf, respectively. Hence, it is expected that very hard tablets can be produced.

Test Example 4

The tablet obtained in Example 7 and a control aqueous solution of the mixture having the same composition [$^{13}$C-urea (75 mg), crystal cellulose (75 mg), light anhydrous silicic acid (2.5 mg), D-mannitol (81.25 mg), polyplasdone (12.5 mg), hydroxypropyl cellulose (2.5 mg) and magnesium stearate (1.25 mg)] were administered to human subjects. The subjects were preliminarily examined by biopsy under an endoscope, as to whether each subject was positive or negative of *Helicobacter pylori*. The tablet was administered together with water of the same volume as the volume of the aforementioned aqueous solution. Immediately after administration, $^{13}CO_2$ in expired air was measured over time. $^{13}CO_2$ in expired air was measured by a mass analyzer specific for $^{13}CO_2$-urea breath test [VG Isochrom-µ G, Fisons Instruments, Co.]. The results are shown in Table 5.

TABLE 5

| Formulation of diagnostic agents | Infection | Time after administration (min) | | | | | | | | |
|---|---|---|---|---|---|---|---|---|---|---|
| | | 0 | 5 | 10 | 15 | 20 | 25 | 30 | 45 | 60 |
| Aqueous solution | not infected | 0 | 9.5 | 3.5 | 1.5 | — | — | 0.5 | 0.5 | 0.5 |
| Aqueous solution | infected | 0 | 15.0 | 14.5 | 12.0 | 13.5 | 11.0 | 12.8 | 11.3 | 10.8 |
| Tablet | not infected | 0 | 1.0 | 0.5 | 0.9 | 0.1 | 1.6 | 1.8 | 1.0 | 1.9 |
| Tablet | infected | 0 | 6.0 | 10.5 | 11.0 | 12.5 | 13.0 | 13.8 | 14.3 | 13.8 |

The figures in the table represent the content of $^{13}CO_2$ (‰) in the whole carbon dioxide in expired air. As apparently shown by the change of the content of $^{13}CO_2$ in the expired air over time in Table 5, it is observed that the content of $^{13}CO_2$ in the expired air from the subjects positive and negative with *Helicobacter pylori* infection after administration of the aqueous solution of $^{13}CO_2$-urea was initially elevated at an early stage of 5 to 10 minutes, but the content in the expired air from the subjects negative with *Helicobacter pylori* infection after administration of the tablet of $^{13}CO_2$-urea was not initially elevated. Accordingly, the influences of oral bacterial flora on the tablet of $^{13}CO_2$-urea can be suppressed so that accurate and rapid diagnosis of the infection can be practiced.

Test Example 5

The tablets produced in Examples 9 and 10 and Reference Example 1 were measured by the same method as in the Test Example 3. The results are shown in Table 6.

TABLE 6

| Tablet composition | Tableting pressure (kgf) | Tablet diameter (mm ø) | Tablet thickness (mm) | Hardness (kgf) | Disintegration time (sec) |
|---|---|---|---|---|---|
| Example 9 | 10 | 8.0 | 3.3 | 22.2 | 82 |
| Example 9 | 15 | 8.0 | 3.0 | 31.1 | 93 |
| Example 9 | 20 | 8.0 | 2.9 | 32.2 | 166 |
| Example 10 | 10 | 8.0 | 3.0 | 20.0 | 222 |
| Example 10 | 15 | 8.0 | 3.0 | 23.5 | 341 |
| Example 10 | 20 | 8.0 | 2.9 | 26.6 | 358 |
| Reference Example 1 | 10 | 8.1 | 3.0 | 6.8 | 246 |
| Reference Example 1 | 15 | 8.1 | 3.0 | 7.0 | 299 |
| Reference Example 1 | 20 | 8.1 | 2.9 | 7.7 | 310 |

These data were statistically treated. If the disintegration time of each tablet is preset at 30 seconds, the tablets of Examples 9 and 10 can procure individually hardness values of 13.6 kgf and 10.1 kgf, respectively, which indicates that the tablets are of larger hardness, but the tablet of Reference Example 1 has hardness of 2.7 kgf, which indicates that the tablet is soft. If the disintegration time of each tablet is preset at 60 seconds, the tablets of Examples 9 and 10 can procure individually hardness values of 19.0 kgf and 11.6 kgf, respectively, which indicate that the tablets are of larger hardness, but the tablet of Reference Example 1 has hardness of 3.2 kgf, which indicates that the tablet is soft. If the disintegration time of each tablet is preset at 120 seconds, the tablets of Examples 9 and 10 can procure individually hardness values of 29.6 kgf and 14.4 kgf, respectively, which indicates that the tablets are of larger hardness, but the tablet of Reference Example 1 has hardness of 4.3 kgf, which indicates that the tablet is soft.

Test Example 6

The tablets produced in Examples 11 and 12 and Reference Example 2 were measured by the same method as in the Test Example 3. The results are shown in Table 7.

TABLE 7

| Tablet composition | Tablet thickness (mm) | Hardness (kgf) | Disintegration time (sec) |
|---|---|---|---|
| Example 11 | 3.35 | 21.2 | 238 |
| Example 11 | 3.40 | 16.8 | 223 |
| Example 11 | 3.45 | 15.0 | 122 |
| Example 11 | 3.50 | 12.9 | 42 |
| Example 12 | 3.35 | 17.5 | 679 |
| Example 12 | 3.40 | 13.9 | 635 |
| Example 12 | 3.45 | 12.4 | 348 |
| Example 12 | 3.50 | 10.7 | 121 |
| Reference Example 2 | 3.25 | 3.0 | 210 |
| Reference Example 2 | 3.30 | 3.1 | 208 |
| Reference Example 2 | 3.35 | 2.9 | 187 |

These data were statistically treated. If the disintegration time of each tablet is preset at 30 seconds, the tablets of Examples 11 and 12 can procure individually hardness values of 11.0 kgf and 8.5 kgf, respectively, which indicates that the tablets are of larger hardness, but the tablet of Reference Example 2 has hardness of 1.4 kgf, which indicates that the tablet is soft. If the disintegration time of each tablet is preset at 60 seconds, the tablets of Examples 11 and 12 can procure individually hardness values of 12.3 kgf and 8.8 kgf, respectively, which indicates that the tablets are of larger hardness, but the tablet of Reference Example 2 has hardness of 1.7 kgf, which indicates that the tablet is soft. If the disintegration time of each tablet is preset at 120 seconds, the tablets of Examples 11 and 12 can procure individually hardness values of 14.9 kgf and 9.6 kgf, respectively, which indicates that the tablets are of larger hardness, but the tablet of Reference Example 2 has hardness of 2.2 kgf, which indicates that the tablet is soft.

Reference Example 1

$^{13}$C-urea (50 g), crystal cellulose (60 g), citric acid anhydride (63 g), croscarmellose sodium (24 g) and magnesium stearate (3 g) were mixed together, and the resulting mixture was then ground by a grinder (Sample Mill Grinder, manufactured by Fuji Paudal, Type KEWG-1F) to a final average particle diameter of 100 μm or less. Then, 200 mg of the mixture powder was pressed at individual pressures of 10, 15 and 20 kgf, by means of a hydraulic pressing machine [P-1B, manufactured by Riken Instruments, Co.] to prepare tablets.

Reference Example 2

$^{13}$C-urea (500 g), crystal cellulose (600 g), citric acid anhydride (630 g), croscarmellose sodium (240 g) and magnesium stearate (30 g) were charged in a V-type blender for mixing therein for 5 minutes, and the resulting mixture was then ground by a grinder (Sample Mill Grinder, manufactured by Fuji Paudal, Type KEWG-1F) to a final average particle diameter of 100 μm or less, followed by tableting by a rotary tableting machine (Correct 12HUK,, manufactured by Kikusui Seisakusho) by means of a mold of 8.5 mm, to prepare a tablet of 200 mg. If the mixture was left to stand without tableting process, the urea was observed to aggregate together. During the process of tableting, a slight degree of sticking was also observed.

EXAMPLES

Examples will be described below.

Example 1

$^{13}$C-urea (1100 g) and light anhydrous silicic acid (100 g) were mixed together, and the resulting mixture was ground by a grinder (Sample NMi Grinder, manufactured by Fuji Paudal, Type KEWG-1F) to a final average particle diameter to 100 μm or less. Then, 300 mg of the mixture powder was pressed by a hydraulic pressing machine (P- 1B, manufactured by Riken Instruments, Co.) to produce a tablet of 300 mg (containing 275 mg of $^{13}$C-urea).

Example 2

$^{13}$C-urea (1000 g) and light anhydrous silicic acid (200 g) were mixed together, and the resulting mixture was ground by a grinder (Sample Mill Grinder, manufactured by Fuji Paudal, Type KEWG-1F) to a final average particle diameter to 100 μm or less. Then, 300 mg of the mixture powder was pressed by a hydraulic pressing machine (P-1B, manufactured by Riken Instruments, Co.) to produce a tablet of 300 mg (containing 250 mg of $^{13}$C-urea.)

Example 3

$^{13}$C-urea (1000 g), crystal cellulose (900 g) and light anhydrous silicic acid (100 g) were mixed together, and the resulting mixture was ground by a grinder (Sample Mill Grinder, manufactured by Fuji Paudal, Type KEWG-1F) to a final average particle diameter to 100 μm or less. Then, 300 mg of the mixture powder was pressed by a hydraulic pressing machine (P-1B, manufactured by Riken Instruments, Co.) to produce a tablet of 300 mg (containing 150 mg of $^{13}$C-urea).

Example 4

$^{13}$C-urea (1000 g), crystal cellulose (1000 g) and light anhydrous silicic acid (30 g) were charged in a V-type blender (Type VI-20, manufactured by Tokuju Kosakusho) for mixing therein for 5 minutes, and the resulting mixture was then ground by a grinder (Sample MU Grinder, manufactured by Fuji Paudal, Type KWG-1F) to a final average particle diameter of 100 μm or less. The ground product was charged into a high-speed agitation tableting machine (Type FM-VG-25P, manufactured by Fuji Industry, Co.), followed by addition of corn starch (307.5 g) and polyplasdon (125 g) and subsequent injection of a 5 w/w % hydroxypropyl cellulose solution in ethanol (500 g) for granulation. The resulting granule product was dried by using a fluidized-bed granulation dryer (Type WSG-5, manufactured by Glatt Co.) at an inlet air temperature of 60° C. for 30 minutes. The dried powder was prepared as a uniform granule through a metal net of No.24, followed by addition of magnesium stearate (12.5 g), for mixing by means of a V-type blender for 3 minutes. The mixture powder was tableted by means of a rotary tableting machine (Correct 12HUK,, manufactured by Kikusui Seisakusho) with a metal mold of 8.5 mm, to prepare a tablet of 250 mg (containing 100 mg of $^{13}$C-urea).

Example 5

$^{13}$C-urea (1000 g) and light anhydrous silicic acid (80 g) were charged in a V-type blender (Type VI-5, manufactured by Tokuju Kosakusho), for mixing therein for 5 minutes, and the resulting mixture was then ground by a grinder (Sample Mill Grinder, manufactured by Fuji Paudal, Type KWG-1F) to a final average particle diameter of 100 μm or less. The ground product was charged into a high-speed agitation tableting machine (Type FM-VG-25P, manufactured by Fuji Industry, Co.), followed by addition of lactose (835 g), crystal cellulose (535 g) and hydroxypropyl cellulose (25 g) and subsequent injection of ethanol (500 g) for granulation. The resulting granule product was dried by using a fluidized-bed granulation dryer (Type WSG-5, manufactured by Glatt, Co.) at an inlet air temperature of 60° C. for 30 minutes. The dried powder was prepared as a uniform granule through a metal net of No.24, followed by addition of magnesium stearate (25 g) and mixing by means of a V-type blender (Type VI-20, manufactured by Tokuju Kosakusho) for 3 minutes. The mixture powder was tableted by means of a rotary tableting machine (Correct 12HUK,, manufactured by Kikusui Seisakusho) with a metal mold of 8.5 mm, to prepare a tablet of 250 mg (corresponding to 100 mg of $^{13}$C-urea).

Example 6

The powder mixed and ground in the same manner as in Example 4 (2030 g), corn starch (307.5 g) and polyplasdone (125 g) were charged in a fluidized-bed granulation dryer (Type WSG-5, manufactured by Glatt, Co.), followed by spraying of an aqueous 5 w/w % hydroxypropyl cellulose solution, to prepare granule products by routine methods. The granule products were prepared as a uniform granule through a metal net of No.24, followed by addition of magnesium stearate (12.5 g), for mixing by means of a V-type blender Type VI-20, manufactured by Tokuju Kosakusho) for 3 minutes. The mixture powder was tableted by means of a rotary tableting machine (Correct 12HUK,, manufactured by Kikusui Seisakusho) with a metal mold of 8.5 mm, to prepare a tablet of 250 mg (containing 100 mg of $^{13}$C-urea).

Example 7

$^{13}$C-urea (750 g), crystal cellulose (750 g) and light anhydrous silicic acid (25 g) were charged in a V-type blender Type VI-20, manufactured by Tokuju Kosakusho) for mixing therein for 5 minutes, and the resulting mixture was then ground by a grinder (Sample Mill Grinder, manufactured by Fuji Paudal, Type KWG-1F) to a final average particle diameter of 100 μm or less. The ground product was charged into a high-speed agitation tableting machine (Type FM-VG-25P, manufactured by Fuji Industry, Co.), followed by addition of D-mannitol (812.5 g) and polyplasdone(125 g) and subsequent injection of a 5 w/w % hydroxypropyl cellulose in ethanol (500 g) for granulation. The resulting granule product was dried by using a fluidized-bed granulation dryer (Type WSG-5, manufactured by Glatt, Co.) at an inlet air temperature of 60° C. for 30 minutes. The dried powder was prepared as a uniform granule through a metal net of No.24, followed by addition of magnesium stearate (12.5 g) and mixing by means of a V-type blender for 3 minutes. The mixture powder was tableted by means of a rotary tableting machine (Correct 12HUK,, manufactured by Kikusui Seisakusho) with a metal mold of 8.5 mm, to prepare a tablet of 250 mg (corresponding to 75 mg of $^{13}C$-urea).

Example 8

$^{13}C$-urea (1000 g) and aluminum hydroxide (1000 g) were charged in a V-type blender for mixing therein for 5 minutes, and the resulting mixture was then ground by a grinder (Sample Mill Grinder, manufactured by Fuji Paudal, Type KWG-1F) to a final average particle diameter of 100 μm or less. The ground product was charged into a high-speed agitation tableting machine, followed by addition of crystal cellulose (805 g) and polyplasdone (150 g) and subsequent injection of a 5 w/w % hydroxypropyl cellulose in ethanol (600 g) for granulation. The resulting granule product was dried by using a fluidized-bed granulation dryer at an inlet air temperature of 60 ° C. for 30 minutes. The dried powder was prepared as a uniform granule through a metal net of No.24, followed by addition of magnesium stearate (15 g) and mixing by means of a V-type blender for 3 minutes. The mixture powder was tableted by means of a rotary tableting machine with a metal mold of 9 mm, to prepare a tablet of 300 mg (containing 100 mg of $^{13}C$-urea).

Example 9

$^{13}C$-urea (167 mg) and light anhydrous silicic acid (33 g) were mixed together, and the resulting mixture was ground by a grinder (Sample Mill Grinder, manufactured by Fuji Paudal, Type XEWG-1F) to a final average particle diameter to 100 μm or less. Then, 200 mg of the mixture powder was pressed by a hydraulic pressing machine (P-1B, manufactured by Riken Instruments, Co.) at individual tableting pressures of 10, 15 and 20 kgf to produce tablets.

Example 10

$^{13}C$-urea (100 g), crystal cellulose (90 g) and light anhydrous silicic acid (10 g) were mixed together, and the resulting mixture was ground by a grinder (Sample Mill Grinder, manufactured by Fuji Paudal, Type KEWG-1F) to a final average particle diameter to 100 μm or less. Then, 200 mg of the mixture powder was pressed by a hydraulic pressing machine (P-1B, manufactured by Riken Instruments, Co.) at tableting pressures of 10, 15 and 20 kgf, to produce tablets.

Example 11

$^{13}C$-urea (1000 g) and light anhydrous silicic acid (200 g) were charged in a V-type blender for mixing for 5 minutes. The resulting mixture was ground by a grinder (Sample MU Grinder, manufactured by Fuji Paudal, Type KEWG-1F) to a final average particle diameter to 100 μm or less, followed by tableting by a rotary-type tableting machine (Correct 12HUK,, manufactured by Kikusui Seisakusho) with a mold of 8.5 mm, to produce a tablet of 200 mg.

Example 12

$^{13}C$-urea (1000 g), crystal cellulose (900 g) and light anhydrous silicic acid (100 g) were charged in a V-type blender for mixing for 5 minutes. The resulting mixture was ground by a grinder (Sample Mill Grinder, manufactured by Fuji Paudal, Type KEWG-1F) to a final average particle diameter to 100 μm or less, followed by tableting by a rotary-type tableting machine (Correct 12HUK,, manufactured by Kikusui Seisakusho) with a mold of 8.5 mm, to produce a tablet of 200 mg.

Industrial Applicability

The tablet of the isotope-labeled urea of the present invention is useful as a diagnostic agent for detecting the infection with urease-producing bacteria, specifically *Helicobacter pylori*. By the method of the present invention, the stickiness of urea can be prevented, so such urea can be formulated into tablets at an industrial scale. The tablet of the present invention has such appropriate hardness that the tablet is hardly worn or broken through the impact during the production or delivery or the tablet is less influenced by urease derived from oral bacterial flora.

What is claimed is:

1. A tablet containing isotope-labeled urea and an inorganic compound, wherein said inorganic compound prevents cohesion of urea due to the stickiness of urea in the tablet, and wherein the tablet is formulated to detect urease-producing microorganism in the stomach.

2. A tablet containing isotope-labeled urea and an inorganic compound,
   wherein the tablet is formulated for detecting urease-producing microorganism in the stomach, and
   wherein said inorganic compound prevents stickiness of urea onto formulation machines during production of the tablet.

3. A tablet containing isotope-labeled urea and an inorganic compound,
   wherein the tablet is formulated for detecting the presence of urease-producing microorganism in the stomach,
   wherein said inorganic compound prevents cohesion of urea due to the stickiness of urea in the tablet, and stickiness of urea onto formulation machines during production of the tablet.

4. A tablet according to any one of claims 1–3, further containing an organic compound.

5. A tablet according to any one of claims 1–3, further containing a disintegrant.

6. A tablet according to any one of claims 1–3, further containing an organic compound and a disintegrant.

7. A tablet according to any one of claims 1–3, wherein the inorganic compound is selected from the group consisting of inorganic compounds containing silica, inorganic compounds containing calcium and inorganic compounds containing aluminum.

8. A tablet according to 4, wherein the organic compound is a sugar.

9. A tablet according to claim 5, wherein the disintegrant is selected form the group consisting of polyplasdone, low-substituted hydroxypropyl cellulose, croscarmellose sodium, carboxymethyl cellulose or the calcium salt thereof, and hydroxypropyl starch.

10. A method for detecting urease-producing microorganism in the stomach, comprising, administering a tablet containing isotope-labeled urea and an inorganic compound, and detecting the isotope-labeled carbon dioxide secreted via exhaled air.

11. A method according to claim 10, wherein the tablet further contains an organic compound.

12. A method according to claim 10, wherein the tablet further contains a disintegrant.

13. A method according to claim 10, wherein the tablet further contains an organic compound and a disintegrant.

14. A method according to any one of claims 10–12, wherein the inorganic compound is selected from the group consisting of inorganic compounds containing silica, inorganic compounds containing calcium and inorganic compounds containing aluminum.

15. A method according to claim 11 or 13, wherein the organic compound is a sugar.

16. A method according to claim 12 or 13, wherein the disintegrant is selected from the group consisting of polyplasdone, low-substituted hydroxypropyl cellulose, croscarmellose sodium, carboxymethyl cellulose or the calcium salt thereof, and hydroxypropyl starch.

17. A process for producing a tablet containing isotope-labeled urea which is used for detecting urease-producing microorganism, comprising,
   mixing an inorganic compound with the isotope-labeled urea to give a mixture, and
   formulating the mixture into a tablet with a formulation machine.

18. A process for producing a tablet containing isotope-labeled urea which is used for detecting urease-producing microorganism, comprising,
   mixing an inorganic compound with the isotope-labeled urea to give a mixture,
   grinding the mixture with grinder to give ground product, and
   formulating the ground product into a tablet with a formulation machine.

19. A process according to claim 18, wherein the particle size of the ground product is 100 μm or less.

20. A process according to any one of claims 17–19, wherein the mixture further contains an organic compound.

21. A process according to any one of claims 17–19, wherein the mixture further contains a disintegrant.

22. A process according to any one of claims 17–19, wherein the mixture further contains an organic compound and a disintegrant.

23. A process according to any one of claims 17–19, wherein the inorganic compound is selected from the group consisting of inorganic compounds containing silica, inorganic compounds containing calcium and inorganic compounds containing aluminum.

24. A process according to claim 20, wherein the organic compound is a sugar.

25. A process according to claim 21, wherein the disintegrant is selected form the group consisting of polyplasdone, low-substituted hydroxypropyl cellulose, croscarmellose sodium, carboxymethyl cellulose or the calcium salt thereof, and hydroxypropyl starch.

26. A tablet containing isotope-labeled urea and an inorganic compound obtainable by mixing the inorganic compound with the isotope-labeled urea to give a mixture, grinding the mixture with a grinder to give ground product, and formulating the ground product into a tablet with a formulation machine,
   wherein the tablet is formulated for detecting urease-producing microorganism in the stomach.

27. A tablet containing isotope-labeled urea and an inorganic compound, obtainable by mixing the inorganic compound with the isotope-labeled urea to give a mixture, grinding the mixture with a grinder to give ground product, and formulating the ground product into a tablet with a formulation machine,
   wherein the particle size of the ground product is 100 μm or less, and the tablet is for detecting urease-producing microorganism in the stomach.

28. A tablet according to claim 26 or 27, further containing an organic compound.

29. A tablet according to claim 27 or 28, further containing a disintegrant.

30. A tablet according to claim 26 or 27, further containing an organic compound and a disintegrant.

31. A tablet according to claim 26 or 27, wherein the inorganic compound is selected from the group consisting of inorganic compounds containing silica, inorganic compounds containing calcium and inorganic compounds containing aluminum.

32. As. A tablet according to 28, wherein the organic compound is a sugar.

33. A tablet according to claim 30, wherein the disintegrant is selected form the group consisting of polyplasdone, low-substituted hydroxypropyl cellulose, croscarmellose sodium, carboxymethyl cellulose or the calcium salt thereof, and hydroxypropyl starch.

34. A tablet according to claim 7, wherein said inorganic compound is selected from the group consisting of silicic acid anhydride, silicic acid, silicate, ortho-silicic acid, meta-silicic acid, meso-disilicic acid, meso-trisilicic acid, meso-tetrasilicic acid, calcium carbonate, calcium hydrogen phosphate, calcium hydroxide, calcium chloride, calcium sulfate, calcium nitrate, aluminum hydroxide and aluminum chloride.

35. A tablet according to claim 34, wherein said tablet has a hardness of 4 kfg or more.

36. A tablet according to claim 35, wherein said tablet has a disintegration time of at least 120 seconds.

37. A tablet containing isotope-labeled urea and an inorganic compound.

38. The tablet according to claim 37, further containing an organic compound.

39. The tablet according to claim 37, further containing a disintegrant.

40. The tablet according to claim 37, further containing an organic compound and a disintegrant.

41. The tablet according to any one of claims 37–40, wherein the inorganic compound is selected from the group consisting of inorganic compounds containing silica, inorganic compounds containing calcium and inorganic compounds containing aluminum.

42. The tablet according to claim 38 or 40, wherein the organic compound is a sugar.

43. The tablet according to claim 39 or 40, wherein the disintegrant is selected from the group consisting of polyplasdon, low-substituted hydroxypropyl cellulose, croscarmellose sodium, carboxymethyl cellulose or the calcium salt thereof and hydroxypropyl starch.

44. The tablet according to any one of claims 37–40, wherein the inorganic compound is selected from the group consisting of inorganic compounds containing silica.

45. The tablet according to claim 44, wherein the inorganic compound is silicic acid anhydride.

46. A tablet according to claim 1, wherein the tablet is formulated such that in the stomach the isotope-labeled urea is degraded to produce a material detected for determining presence of urease-producing microorganism in the stomach.

47. A tablet according to claim 2, wherein the tablet is formulated such that in the stomach the isotope-labeled urea is degraded to produce a material detected for determining presence of urease-producing microorganism in the stomach.

48. A tablet according to claim 3, wherein the tablet is formulated such that in the stomach the isotope-labeled urea is degraded to produce a material detected for determining presence of urease-producing microorganism in the stomach.

49. A method according to claim 10, wherein the tablet is formulated such that in the stomach the isotope-labeled urea is degraded to produce the isotope-labeled carbon dioxide, which is detected for determining presence of urease-producing microorganism in the stomach.

50. A process according to claim 17, wherein the tablet is formulated such that in the stomach the isotope-labeled urea is degraded to produce a material detected for determining presence of urease-producing microorganism in the stomach.

51. A process according to claim 18, wherein the tablet is formulated such that in the stomach the isotope-labeled urea is degraded to produce a material detected for determining presence of urease-producing microorganism in the stomach.

52. A tablet according to claim 26, wherein the tablet is formulated such that in the stomach the isotope-labeled urea is degraded to produce a material detected for determining presence of urease-producing microorganism in the stomach.

53. A tablet according to claim 27, wherein the tablet is formulated such that in the stomach the isotope-labeled urea is degraded to produce a material detected for determining presence of urease-producing microorganism in the stomach.

54. A tablet according to claim 1, containing the inorganic compound in an amount of 0.1 to 200 parts by weight of the isotope-labeled urea.

55. A tablet according to claim 54, which contains 2–2,000 mg isotope-labeled urea.

56. A method according to claim 10, containing the inorganic compound in an amount of 0.1 to 200 parts by weight based on 100 parts by weight of the isotope-labeled urea.

57. A process according to claim 17, wherein the mixture contains the inorganic compound in an amount of 0.1 to 200 parts by weight based on 100 parts by weight of the isotope-labeled urea.

* * * * *